Figure 1:
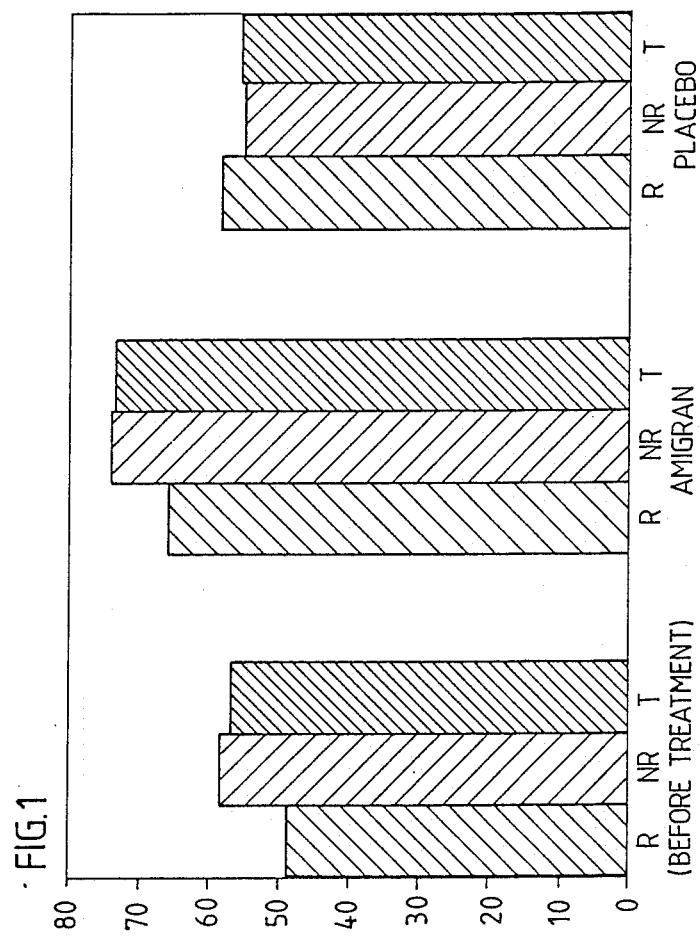

United States Patent [19]

Hamberger et al.

[11] Patent Number: 4,962,121

[45] Date of Patent: Oct. 9, 1990

[54] METHOD AND COMPOSITION FOR TREATING NEUROLOGICAL DISEASES SUCH AS MIGRAINE

[76] Inventors: Anders Hamberger, Torpedgatan 4B, S-421 76, Västra Frölunda, Sweden; Nico M. Van Gelder, 59, Fountain Drive, Dollard des Ormeaux, Quebec, Canada, H9B 1X9

[21] Appl. No.: 184,341

[22] Filed: Apr. 21, 1988

[30] Foreign Application Priority Data

Apr. 22, 1987 [SE] Sweden ................................ 8701662

[51] Int. Cl.$^5$ ............................................. A61K 31/40
[52] U.S. Cl. ..................................................... 514/419
[58] Field of Search ......................................... 514/419

[56] References Cited

U.S. PATENT DOCUMENTS

| | | | |
|---|---|---|---|
| 4,303,692 | 12/1981 | Gaull | 426/801 |
| 4,434,160 | 2/1984 | Jeretin et al. | 514/567 |
| 4,439,452 | 3/1984 | Ehrenpreis et al. | 424/319 |
| 4,629,625 | 12/1986 | Gaull | 514/905 |
| 4,687,782 | 8/1987 | Brantman | 514/562 |
| 4,725,427 | 2/1988 | Ashmead et al. | 514/905 |
| 4,753,926 | 6/1988 | Lucas et al. | 426/801 |

OTHER PUBLICATIONS

Tomichek et al., "Role of Vitamines in Taurine Synthesis from Sulfate by the Chick," J. Nutr. 102: 313–318 (1972).

Bland, *Octacosanol, Cornitine, and other Accessory Nutrients*, pp. 4–13 (1982).

Duke, S. F., *The Chemistry of the Vitamins*, p. 75 (1965).

*Primary Examiner*—Sidney J. Friedman
*Attorney, Agent, or Firm*—Ostrolenk, Faber, Gerb & Soffen

[57] ABSTRACT

A method and composition is described for treating neurological diseases such as migraine, by influencing the nerve cells. This is achieved by optimizing the ability of the nerve cell gliacytes to transport taurine and the ability of the nerve cells to absorb taurine, by the external supply of amino acids occurring normally in the body. Preferred compositions include taurine, L-carnitine, zinc gluconate and calcium glycerophosphate.

13 Claims, 3 Drawing Sheets

METHOD AND COMPOSITION FOR TREATING NEUROLOGICAL DISEASES SUCH AS MIGRAINE

The present invention relates to a method and a composition for treating neurological diseases and is particularly advantageous for use in treating migraine. In the following description the invention will be described with reference to the treatment of migraine without, however, being limited to that specific application.

Recent research into neurological diseases manifested in the form of attacks at irregular intervals has given increased insight into the underlying mechanisms of such diseases, showing particularly that the genetic or inherited tendency to attacks is only noticeable when the metabolic state of the brain is also contributory thereto. It is not unusual when registering a person's brain activity electrically (EEG), to detect an abnormality which can be characterised as a predisposition for such attacks. However, the person in question may never have experienced such problems. Migraine is an example of this, and often occurs unpredictably. There is often some advance warning of migraine attacks and the attacks are followed by a period of tiredness and not infrequently by a normal headache, factors indicating that the nerve system has been over-activated during the attack. Experimental research into migraine is handicapped since there are no studies on animals. However, progress made in measuring and analysis techniques over the last five-year period has increased the possibility of registering attacks suffered by patients.

The triggering mechanism for migraine attacks is considered by many to be a contraction of the blood vessels, as well as extensive aggregation of thrombocytes, a type of small blood platelet.

The aggregation causes changes in the distribution of a number of important substances between the actual blood platelet and the free liquid constituting the blood. Since it is this phase which can equilibrate with the organs of the body, e.g. the brain, therefore, disturbances probably also occur in the supply of substances from the blood. Regardless of whether the attack is initiated by the vessels or starts in the brain itself, the effect is the same—a certain ischemia (oxygen deficiency) and excitation of the nerve cells occurs, and the increased concentration of exciting signal substances will be found around the nerve cells in the interstitium (extracellular space).

An important mechanism for removing the excitation signal substances is absorption in the gliacytes, i.e. the help-cells pertaining to the nerve cells, which are vital to the function of the brain and which actually take up half the volume of the brain. The gliacytes easily detect the degree of activity in the nerve cells and perform their "fire brigade" function in various ways. One such way is to accumulate the excitatory signal substances and convert them to glutamine, a substance which is harmless to the nerve cells. This causes increased water absorption in the gliacytes and the gliacytes can reduce this by pumping out glutamine to the blood. Another component in the protective function of the gliacytes is the release of taurine, the nerve cells being "showered" with this substance which is an inhibitorial signal substance, i.e. it has exactly the opposite effect to the excitatory signal substances mentioned above, which contributes to the migraine attack.

A number of known substances have previously been used to alleviate migraine. Some of these alleviate a migraine attack which has already started, whereas others prevent attacks However, no known composition is completely satisfactory and several also have undesired and sometimes dangerous side effects.

Ergotamine or ergot has been used to alleviate migraine for the last hundred years. This preparation causes strong contraction of the blood vessels, thus preventing the increased blood flow which causes headaches. Ergotamine is most effective if used before an attack of migraine. Protracted use or over-dosage entails the risk of impaired circulation in the hands and feet.

Pain-killers such as aspirin (acetylsalicylic acid) are the medicine most often resorted to, but relief is only moderate. They act partly by relieving the pain and partly by preventing the formation of the substances which damage cells in blood vessels and brain. However, these pain killers often give side effects in the form of stomach complaints.

Beta-blockers, used extensively in cases of hypertension and cardiac complaints, have in many cases been found to give good results in relieving migraine. As in the case of ergotamine, this group of pharmaceuticals probably acts by preventing expansion of the blood vessels, but biochemically they may act directly on the brain cells. The disadvantage is that beta-blockers affect both blood pressure and pulse, and result in tiredness, increased weight and other side effects.

Tranquilizers and anti-depressants are sometimes also used to relieve migraine, but the risk of addiction limits their usability.

It has now surprisingly been found possible to avoid the drawbacks mentioned above in the known treatment of migraine, for instance, by means of the method according to the present invention substantially comprising optimizing the nerve cell gliacytes by the external supply of amino acids occurring normally in the body.

Experiments have shown that taurine is released with delayed reaction after excitation and through the previous specific damage it can be proved that this release takes place from the gliacytes. Taurine is an amino acid which is important to the development of the nervous system. Gliacytes do not produce their own taurine, but obtain it from the blood, and the blood obtains it from the stomach and intestines.

Strong excitation, stress on the nerve cells, places increased demands on the function of the gliacytes, one of these demands being to release more taurine to the nerve cells. If there is a deficiency of taurine in the blood at the time, taurine deficiency will also occur in the gliacytes. Excitation of the nerve cells is therefore less controlled and this mechanism will cause increased water absorption in the gliacytes, which also require taurine for their osmoregulation. Several factors thus combine to cause stress in the gliacytes. The increased water absorption causes the whole brain to swell, brain oedema to occur causing increased pressure in the brain and a pull and pressure on the brain membranes and walls of the large blood vessels. These structures contain pain receptors, not present in the tissue of the brain. Pain localized to the head is consequently usually triggered from the walls of the membranes and blood vessels. Similarly increased accumulation of liquid is probably also obtained in organs other than the brain but it is only the brain which is enclosed in an unyielding cavity of bone. The increased excretion of urine experienced by many migraine patients towards the end of an attack cannot come only from the brain and it is of course also possible that the diarrhoea experienced by many after an attack of migraine is not only triggered neuronally.

Through the invention, therefore, optimization of the function of the gliacytes is achieved and the nerve cells in particular make use of glucose as substrate for maximum energy recovery, while the gliacytes make best use of leucine and glycerophosphate. Only when the gliacytes are optimally equipped from the general energy aspect can they pump water maximally. At the same time it is important that the free concentration of taurine in the blood is sufficient to guarantee saturation of the glial taurine pool.

According to the invention, therefore, the gliacytes are caused to function optimally by making use of the glycerophosphate supplied.

According to a preferred embodiment of the invention, carnitine is also added to counteract the risk of inexplicable taurine losses under certain conditions.

According to another embodiment of the invention the external supply of amino acids also includes the simultaneous supply of zinc, calcium and/or pyridoxalphosphate to achieve synergetic effects on membrane surfaces and in the cell liquid of the nerve cells.

Experiments have indicated that the taurine function in the nerve system is associated with zinc in a manner which has been relatively unknown until now. Similarly the taurine function is related to calcium, as well as taurine absorption in stomach and intestines being found to increase through the addition of glycine.

According to yet another embodiment of the invention, treatment may also include the supply of histidine and proline. These amino acids are significant for maintaining structural proteins in the nerve cells, particularly in the outgrowth membranes. Histidine and pyridoxalphosphate are essential histamine regulators in the brain.

Several of the components mentioned above, such as taurine, histidine and calcium, have an effect on the nervous system and also an important stabilizing function on heart and blood vessels, which may contribute to reducing the vascular cramps possibly inducing migraine.

The invention also relates to a composition for treating neurological diseases, such as migraine, by influencing the nerve cells. Characteristic of the composition is that it contains amino acids occurring normally in the body, in order to optimize the ability of the nerve cell gliacytes to transport taurine and the ability of the nerve cells to absorb taurine.

According to a preferred embodiment, the composition includes one or more of the substances selected from the following group: calcium glycerophosphate, taurine, glycine, L-leucine, orthophospho-L-serine, L-carnitine (HCl), pyridoxal (as phosphate), zinc (as gluconate), histidine and proline.

The invention will be further described in the following with reference to the Examples below:

Example 1

A composition is prepared by forumulating the following components:

| | |
|---|---|
| Calcium glycerophosphate | 1.0 g |
| Taurine | 0.50 g |
| Glycine | 0.08 g |
| L-Leucine | 0.33 g |
| L-carnitine | 0.10 g |

-continued

| | |
|---|---|
| Pyridoxal phosphate | 0.09 g |
| Zinc gluconate | 0.057 g |

The daily dose of this composition is in most cases 2 g, taken as half in the morning and half in the evening to ensure a somewhat better blood level. The composition is best administered as the powder slurred in a small amount of water (150–200 ml)

Example 2

The composition of Example 1 is modified by the incorporation of

| | |
|---|---|
| Caffeine | 0.22 g |
| Aceylsalicylic acid | 1.10 g |

The daily dose of this composition is preferably 3.2 g. 1.6 g is slurried in 100–150 ml of water and taken in the morning and a similar slurry in the evening.

The effect of caffeine on vascular headaches occurring in migraine is due to its contracting effect on the blood vessels of the head. Acetylsalicylic acid inhibits the aggregation of thrombocytes in the blood which is a known factor in the development of migraine attack.

Example 3

A water based solution is advantageous for children and athletes in action. A suitable solution which contains half the daily dose in 25 ml of water is made by dissolving 38.2 g of the composition in Example 1 in 1000 ml water. The powder mixture dissolves within a few minutes with moderate agitation of the vessel. The resulting solution has a light green-yellow colour.

Example 4

An effervescent tablet of the invention is prepared by tabletting the following composition:

| | |
|---|---|
| Calcium glycerophosphate | 225 mg |
| Taurine | 112.5 mg |
| Glycine | 18.75 mg |
| L-leucine | 75 mg |
| L-carnitine | 23 mg |
| Pyridoxal phosphate | 2.25 mg |
| Zinc gluconate | 13.75 mg |
| Citric acid | 550 mg |
| Sodiumhydrogencarbonate | 1250 mg |

The tablet may optionally also include:

| | |
|---|---|
| Acetylsalicylic acid | 500 mg |

These effervescent tablets are particularly effective in the treatment of the imminent attack of migraine.

Example 5

The following components are mixed and tabletted to give pressed tablets containing per tablet:

| | |
|---|---|
| Calcium glycerophosphate | 225 mg |
| Taurine | 112.5 mg |
| Glycine | 18.75 mg |
| L-leucine | 75.0 mg |
| L-carnitine HCL | 23.0 mg |
| Pyridoxal phosphate | 2.25 mg |

| | |
|---|---|
| (vitamin B6) | |
| Zinc gluconate | 13.75 mg |

Lactose, microcrystalline celluse E460 and magnesium stearate E572 are mixed in as additives to improve the tabletting properties of the composition. The tablets should be kept in a dry atmosphere in order to avoid development of brown spots (harmless but unpleasant). The normal dosage is two tablets in the morning and two in the evening.

However, this tablet has a fairly "coarse" surface and a diameter of approximately 12 mm. This makes the tablet difficult to swallow for some persons. Consequently, a more agreeable surface material may be coated onto the tablet to improve its palatability.

Example 6

Suppositories may be of great advantage in migraine treatment as the affected person may be completely unable to swallow or digest. These are prepared using the same composition as in Example 5 and using petrolatum, glycerol or a waterbased vehicle to formulate the suppository.

Example 7

Parenteral administration is desirable for intensive use of the invention. A parenterally acceptable aqueous solution is prepared containing:

| | |
|---|---|
| Calcium glycerophosphate | 3.5 g/l |
| Taurine | 6.0 g/l |
| Glycine | 4.6 g/l |

Example 8

The therapeutic concept. In may cases the following simplified composition of the invention may be used. The example below is the amount in a tablet to be taken 3-4 times daily. Additives should be used for tablet manufacturing as described under Example 5.

| | |
|---|---|
| Calcium glycerophosphate | 225 mg |
| Zinc gluconate | 13.75 mg |
| L-carnitine | 23 mg |
| Taurine | 112.5 mg |

Example 9

A composition was prepared by formulating the following components in the stated proportions by weight:

| | |
|---|---|
| Calcium glycerophosphate | 150 |
| Taurine | 75 |
| Glycine | 12.5 |
| L-leucine | 50 |
| O-phospho-L-serine | 12.5 |
| L-carnitine (HCl) | 12.5 |
| Pyridoxal (as phosphate) | 1.5 |
| Zinc (as gluconate) | 1.25 |
| Histidine | 12.5 |
| Proline | 12.5 |

Experiments using the above composition for treating migraine show that the preparation does not affect the normal triggering factors for migraine. The difference is that the brain cells are now able to pump out the water. The first result noted after treatment for one to two weeks is considerable relief from pain and that the pain disappears completely after 4-5 hours and the patient is capable of working again. Complete freedom from attacks is achieved after a few weeks.

Two or three tablets of the composition a day (each tablet containing the amounts stated as mg amounts) has been found to be a suitable dose during the build-up stage. Once the desired result has been obtained after a few weeks, the dose can be reduced to 2-3 tablets every second or third day. So far all patients treated With the preparation have reported a distinct improvement, total freedom from migraine. The preparation according to the invention is administered in the form of a diet supplement.

Description of clinical trial

The aim of the treatment is to antagonise oedema in the glial cells of the brain, i.e. water accumulation in those cells which support the neurons. A few neurological conditions are, according to our experience and research characterised by glial oedema during the acute phase. This leaves chronic and microscopically demonstrable changes in the glial cells. The group of conditions primarily caused by glial oedema are some types of epilepsy, most forms of migraine and certain forms of tremor. The biochemical research of developing changes in the water content of the brain has focussed the interest on the importance of certain amino acids which are included in the present preparation. This can be described as a basic therapeutic concept, in which the four components, zinc-taurine-L-carnitine and Ca-glycerophosphate are the main part of the preparation. As additional components, glycine, leucine and pyridoxal phosphate support and strengthen the action of the components of the therapeutic concept.

It is vital to realise that in this area of treatment, the body is supported only with compounds which are normally supplied with the diet and are manufactured by the body systems. Thus, the disease conditions appear mostly as a result of defects in the absorption and/or in the autogenous biosynthetic machineries. Age, sex, weight, body composition etc., are obviously important for the recommended dose, serum levels can be of certain help in establishing some of these deficits. The statistically significant effect of the preparation in a double blind placebo-controlled cross-over study on migraine sufferers in the Neurological Clinic in the University Hospital in Gothenburg (16 cases), described below, is strongly supportive of the experimental evidence.

Methods

Sixteen patients (12 female, 4 male, mean age 42 years) with common migraine (unilateral paroxysmal pulsating headache with anorexia and/or vomiting but without aura) were included in the study. They all had a severe migraine and had been in contact with a neurologist at the University Hospital for several years. Possible migraine precipitating factors had been eliminated as far as possible. Patients with a significant tension headache as well were excluded from the study. The amino acid preparation ("Amigran") and identical appearing placebo tablets were coded by the hospital pharmacist and given in a double-blind randomised manner with the drug and placebo administered in a random order during two two-month periods separated by a one week wash-out period. The dosage was 3 tablets b.i.d. This disage has been decided after an open dose increase study in 5 patients. One tablet of "Amigran" contained 150 mg calcium glycerophosphate, 75 mg taurine, 12.5 mg glycine, 50 mg l-leucine, 12.5 mg l-carnitine (HCl), 1.5 mg pyridoxal phosphate and 1.25 mg zinc gluconate.

The patients recorded in their headache calendar the number of attacks of headache, their severity and the "quality of life" on a 100 mm analogue scale before entering the study and weekly during the study. The calenders were collected each month. The patients were seen by a nurse monthly and by a neurologist before the study and after each test period. The patients also kept a record of the consumption of analgesics or ergot drugs, used during attacks. There was no change in the prescription before the start of the trial and after one month with the drug or placebo.

Amino acids were measured with liquid chromatography after precolumn derivatisation with o-phtaldialdehyde (OPA) according to Lindroth and Mopper (1979). The derivatives were separated on a 5 um Nucleosil C-18 column with gradient elution, i.e. increasing methanol 30–100% in sodium phosphate buffer (50 mM, pH 5.25). Calibration was done with peak height against standard solutions.

Statistical analysis was performed with paired Student's T-statistics and ANOVA. Taurine measurements were analysed by non-paired T-statistics.

Results

Before decoding the study, the patients were asked for possible preferences with respect to the treatment (first or second period). Out of the 16 patients, 7 declared that they had experienced a marked positive effect with the active drug. None declared placebo as the best drug and the remaining 9 patients could not discern any differences in effect between the two treatment periods. The 7 subjectively improved patients had a decrease in headache frequency (FIG. 1) and an improved "quality of life" (FIG. 2).

The 9 remaining patients did not experience a difference between the two treatment periods. Their number of migraine attacks and their "quality of life" rating was not significantly different between the two drug periods. However, the "non-responder" group showed an improved "quality of life" irrespective of tablet used, compared to before entering the study. The correlation between the "quality of life" rating and the number of migraine attacks was good for both groups of patients.

Figure 3:
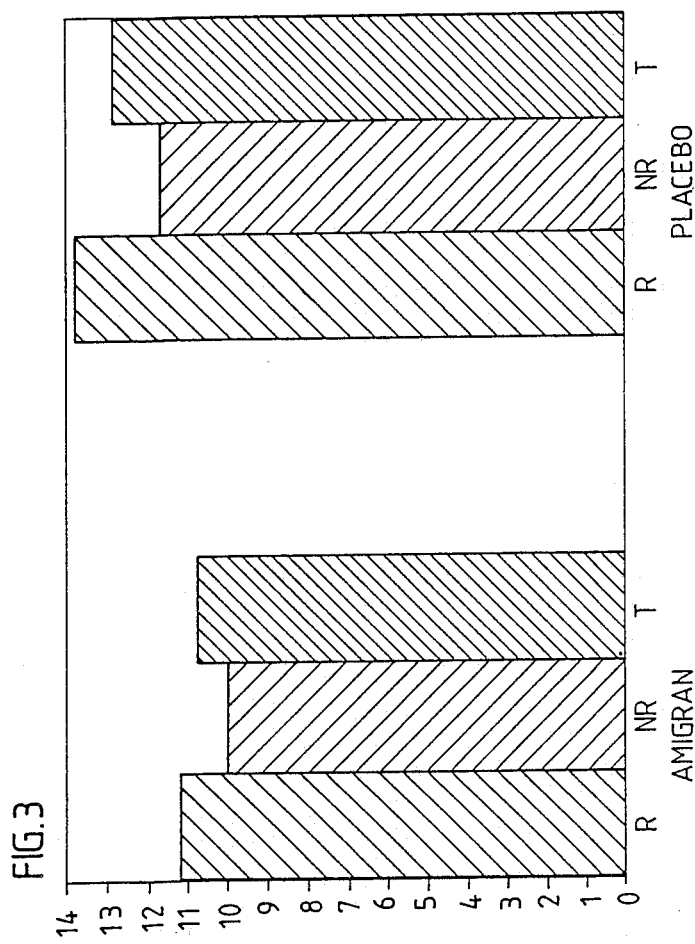

Serum taurine levels were higher during the "Amigran" treatment period than during placebo treatment or before treatment (FIG. 3). There was no difference with respect to serum levels of taurine between "responders" and "non-responders".

There were no side-effects during any of the treatment periods. No patient withdrew from the study during treatment.

Changes in migraine frequency during the second month of the trial are set out in Table 1.

Discussion

Migraine is a common condition, affecting 10–20% of all men and 20–30 of women. Only about 10 of these have a "classical" migraine with irritative symptoms from the CNS preceding the headache phase. The remaining majority have a usually unilateral, pulsating headache often combined with anorexia and vomiting. It can frequently be provoked by emotional or physical stress, certain food, drugs as well as changed hormonal status.

In the overwhelming majority of patients, the condition is self-limiting. If drugs are to be used, simple analgesics with or without sedatives are used. Only a small proportion of migraine sufferers, probably less than 10%, have so frequent attacks, more than 3–4 per month, that continuous prophylactic treatment can be indicated. Of these, about 25–50% respond to beta-adrenoreceptor blocking agents, clonidine or, in the female, gestagen hormones. In the remaining population of severe migraine sufferers and in those with intolerable side-effects from the conventional drugs, there is a lack of alternative medications with lack of severe side-effects but with therapeutic effect.

Preparations of feverfew have been tried in the last years, but side-effects, especially perioral and intraoral ulcerations are common and has forced the withdrawal of the preparation from the Swedish market.

Then asked to make a trial on a preparation available on the market as a non-licensed drug, we chose a set of patients with very frequent migraine without continuous intake of ergot alkaloids or analgesics. All patients had failed on trials with beta-adrenoreceptor blocking agents or clonidine or had had intolerable side-effects of these drugs. All patients had no significant contribution to their headache by tension headache.

In this population of 16 patients, 7 had a significant subjective effect of the active preparation, compared to placebo. None preferred placebo to the active drug. When looking on the subsets of responders with subjective improvement on active drug to placebo and non-responders, with no subjective difference in effect by any preparation, it became evident that the responder group had an increase in life quality and a decrease in the number of attacks per month, compared both to placebo and to pre-study numbers. In the non-responder group, there was also an increase in life quality and a decrease in attack frequency, but this group also showed this response to placebo, compared to pre-study numbers. Hence, the major difference between the responder and the non-responder groups was that both had a better life quality and a decrease in attack frequence on the active drug, but in the non-responder group, there was also a placebo response.

There was no carry-over effect, by statistics, although the attack frequency was lower in those turning from active to placebo than those turning from placebo to active drug, during 3 weeks into the next period, in spite of the one-week wash-out period.

Taurine was thought by us to be the most probable effective component, if any, explaining a possible effect, and was therefore measured in serum. There was a significant increase in serum taurine levels during treatment with the active drug, compared to pre-study levels and the levels during placebo treatment. There was, however, no difference between responders and non-responders with respect to serum taurine levels. This does not by necessity imply that taurine is not the major active principle of the drug, as actually there was a decrease in attacks in the whole population of patients on the active drug.

The amounts of taurine given in this study is only a small fraction of that which has been given e.g. in hypertension, where there is a decrease in the release of epinephrine in treated patients. We did not measure epinephrine, nor any biogenic amine metabolites, so it is hitherto unknown whether the response to the drug might be on the same ground as in borderline hypertension, where the possible active mechanism probably resides in a decrease in the release in the stress hormone.

TABLE 1

Changes in Migraine Frequency in the Second Month During Amigran Therapy

| Patient | Migraine Frequency (Mean No. per Month) | |
| --- | --- | --- |
| | Placebo | Amigran |
| 1 | 17 | 9 |
| 2 | 15 | 12 |
| 3 | 10 | 3 |
| 4 | 28 | 12 |
| 5 | 11 | 3 |
| 6 | 9 | 7 |
| 7 | 7 | 11 |
| 8 | 5 | 8 |
| 9 | 8 | 8 |
| 10 | 14 | 17 |
| 11 | 15 | 24 |
| 12 | 14 | 8 |
| 13 | 15 | 9 |
| 14 | 16 | 12 |
| 15 | 16 | 12 |
| 16 | 16 | 12 |

Figure 2:
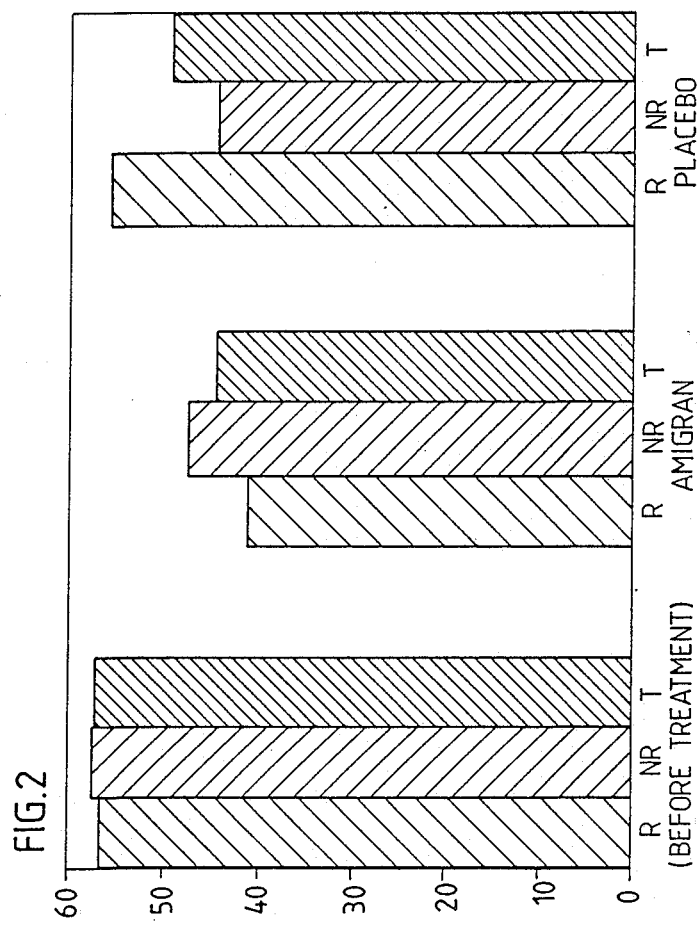

In the accompanying drawings FIGS. 1-3 illustrate results from the clinical trial, as follows:

FIG. 1 : The attack frequency per month during treatment with Amigran and placebo respectively.

R=Patients with subjective improvement by Amigran ("Responders")

NR=Patients without difference in effect between Amigran and placebo ("Non-Responders")

T=Total material

FIG. 2 : Trouble points on a 100 mm analogue scale before treatment, and mean value during two months of treatment with Amigran and placebo respectively R=Responders NR=Non-Responders T=Total material FIG. 3 : Serum taurine before treatment and after one month of treatment with Amigran and placebo respectively R=Responders, (n=7)

NR=Non-Responders,

T=Total

We claim:

1. A method of treating migraine, comprising administering at least one amino acid selected from the group consisting of taurine, glycine, leucine, carnitine, histidine and proline, in an amount effective to optimize the ability of the nerve cell gliacytes to transport taurine and the ability of the nerve cells to absorb taurine.

2. A method according to claim 1, wherein at least one said amino acid is leucine.

3. A method according to claim 1, wherein at least one said amino acid is taurine.

4. A method according to claim 3, wherein the taurine is administered in an amount such that the free concentration of taurine in the blood is maintained at a level effective to assure saturation off the glial taurine pool.

5. A method according to claim 1, wherein at last one said amino acid is carnitine.

6. A method according to claim 1, wherein said amino acids ar histidine and proline.

7. A method according to claim 1, wherein there is also administered at least one substance selected from the group consisting of, zinc, calcium and pyridoxal phosphate.

8. A pharmaceutical composition according to claim 1, comprising the following components in the given proportions by weight.

| | |
| --- | --- |
| Calcium glycerophosphate | 150 |
| Taurine | 75 |
| Glycine | 12.5 |
| L-leucine | 50 |
| O-phospho-L-serine | 12.5 |
| L-carnitine (HCl) | 12.5 |
| Pyridoxal (as phosphate) | 1.5 |
| Zinc (as gluconate) | 1.25 |
| Histidine | 12.5 |
| Proline | 12.5 |

9. A pharmaceutical composition according to claim 1, in the form of a diet supplement.

10. A pharmeceutical composition according to claim 1 in unit dosage form.

11. A pharmaceutical composition according to claim 1 in the form of an effervescent tablet.

12. A pharmaceutical composition according to claim 1 in the form of an aqueous slurry.

13. A method according to claim 1, wherein glycerophosphate is also administered.

* * * * *